United States Patent
Chan et al.

(10) Patent No.: US 8,835,658 B2
(45) Date of Patent: Sep. 16, 2014

(54) ASYMMETRIC SYNTHESIS OF NORCANTHARIDIN ANALOUGUS BY ALKYNYLATION OF OXABENZONORBORNADIENES AND THEIR ANTICANCER ACTIVITIES

(71) Applicants: Hong Kong Baptist University, Kowloon (HK); Yunnan University of Nationalities, Yunnan (CN)

(72) Inventors: Albert Sun-Chi Chan, Kowloon (HK); Baomin Fan, Yunnan (CN); Jun Wang, Yunnan (CN); Chengyuan Lin, Yunnan (CN); Chao Huang, Yunnan (CN); Qingjing Yang, Yunnan (CN); Jianbin Xu, Yunnan (CN); Zhaoxiang Bian, Kowloon (HK); Aiping Lu, Yunnan (CN); Jun Hu, Yunnan (CN)

(73) Assignees: Hong Kong Baptist University, Kowloon (HK); Yunnan University of Nationalities, Yunnan (CN)

( * ) Notice: Subject to any disclaimer, the term of this patent is extended or adjusted under 35 U.S.C. 154(b) by 0 days.

(21) Appl. No.: 13/729,479

(22) Filed: Dec. 28, 2012

(65) Prior Publication Data
US 2014/0187801 A1    Jul. 3, 2014

(51) Int. Cl.
*C07D 307/00*    (2006.01)
*C07D 493/08*    (2006.01)

(52) U.S. Cl.
CPC .................................. *C07D 493/08* (2013.01)
USPC ......................................................... 549/459

(58) Field of Classification Search
USPC ......................................................... 549/459
See application file for complete search history.

(56) References Cited

PUBLICATIONS

Shibata et al, Rh-Catalyzed Enantioselective Cycloadd. of Alkynyl Esters and Norbornene Derivatives, Org. Let. vol. 8 No. 7 pp. 1343-1345 (2006).*

Fan et al., Ligand-Controlled Enantioselective [2+2] Cycloaddition of Oxabicyclic Alkenes with Terminal Alkyns Using Chiral Iridium Catatlysts, Organic Letters, vol. 12, No. 2, p. 304-306 (2010), published online Dec. 21, 2009.

* cited by examiner

*Primary Examiner* — Andrew D Kosar
*Assistant Examiner* — Raymond Covington
(74) *Attorney, Agent, or Firm* — Renner Kenner Greive Bobak Taylor & Weber

(57) ABSTRACT

The present invention relates to a type of norcantharidin analogues and a method to synthesis such norcantharidin analogues by transition metal-catalyzed alkynylation of 7-oxabenzonorbornadienes. The present invention also relates to the use of such norcantharidin analogues in manufacture of a medicament for the treatment of cancer tumors.

6 Claims, No Drawings

ASYMMETRIC SYNTHESIS OF NORCANTHARIDIN ANALOUGUS BY ALKYNYLATION OF OXABENZONORBORNADIENES AND THEIR ANTICANCER ACTIVITIES

FIELD OF THE INVENTION

The present invention relates to a type of norcantharidin analogues and a method to synthesis such norcantharidin analogues.

BACKGROUND OF THE INVENTION

Natural products are a rich source of small molecules provided and inspired many drugs, particularly in the treatment of infectious diseases, cancers, hypercholesterolemia and immunological disorders. Cantharidin (1), in the form of the dried body of the Chinese blister beetles: *Mylabris phalerata* or *M. cichorii*, displays antitumor activity and induces apoptosis in many types of tumor cells. Cantharidin has been used as an anticancer agent by the Chinese for the treatment of hepatoma and esophageal carcinoma for a long time. Although cantharidin is a natural toxin that possesses potent anti-tumor properties, its clinical application is limited due to severe side-effects and highly toxic nature. Norcantharidin (2), the demethylated form of cantharidin has strong anticancer activity, and eliminates some side-effects in the urinary system, does not cause myelosuppression and increases the number of white blood cells. Although norcantharidin has improved activity and toxicity, the effects routinely do not satisfy the current clinical need. Exploring better analogues is vital for changing the current situation, but norcantharidin is a good lead compound.

Scheme 1 The structure of cantharidin and norcantharidin

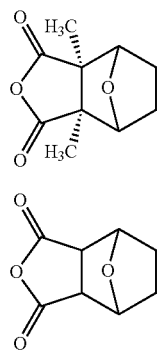

Though numerous analogues of cantharidin and norcantharidin have been synthesized chemically and showed potential anticancer activities, there is little success on clinical application because of the potential toxicity of cantharidin and norcantharidin derivates. The present invention is to describe a method to synthesis of a type of novel norcantharidin analogues by transition metal-catalyzed alkynylation of 7-oxabenzonorbornadienes, and further discuss their bioactivities on tumour cells.

Citation or identification of any reference in this section or any other section of this application shall not be construed as an admission that such reference is available as prior art for the present application.

SUMMARY OF THE INVENTION

Accordingly, it is an object of the present invention to provide a type of novel norcantharidin analogues. The norcantharidin analogues comprise the structure of compound 5:

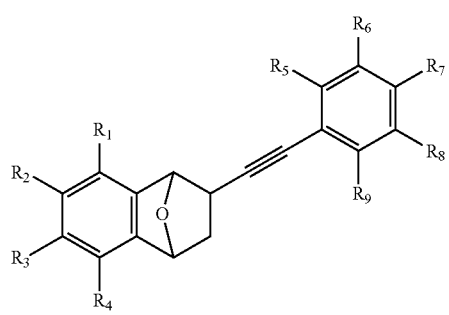

wherein $R_1$, $R_2$, $R_3$, $R_4$ can be selected from Hydrogen, halogen, alkyl, alkenyl, alkynyl, hydroxyl, alkoxyl, amine, nitro, alkylthio, heteroalkyl, and wherein $R_5$, $R_6$, $R_7$, $R_8$, $R_9$ can be selected from hydrogen, halogen, alkyl, alkenyl, alkynyl, hydroxyl, alkoxyl, amine, nitro, nitrile, alkylthio, trifluoromethyl, alkyl sulfonyl, aryl sulfonyl.

A second embodiment of this invention provides a method to synthesis such norcantharidin analogues. The method comprises a step of alkynylation of oxabenzonorbornadienes in the presence of a catalyst.

A third embodiment of the present invention provides the use of such norcantharidin analogues in manufacture of a medicament for the treatment of cancer tumors.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

DETAILED DESCRIPTION OF THE PREFERRED EMBODIMENTS

The present invention is not to be limited in scope by any of the specific embodiments described herein. The following embodiments are presented for exemplification only.

The present invention discloses a type of novel norcantharidin analogues and a method to synthesis such norcantharidin analogues by transition metal-catalyzed alkynylation of 7-oxabenzonorbornadienes, and their bioactivities on tumour cells.

The transition metal-catalyzed reactions of oxabenzonorbornadienes have attracted continuous interest and extensive study in recent years. The addition of terminal alkynes is one of the most important carbon-carbon bond formation reactions. In the presence of different catalysts or under different reaction conditions, oxabenzonorbornadienes and terminal alkynes can take place many different reactions, leading to various compounds, and more complicated products are obtained by the multiple-component addition reactions. In one embodiment of the present invention, it is realized that non-cyclized addition reaction by a Iridium/ligand catalyzed hydroalkynylations of oxabenzonorbornadienes.

Scheme 2 Ir/ligand-catalyzed alkynylation of 7-oxabenzonorbornadienes

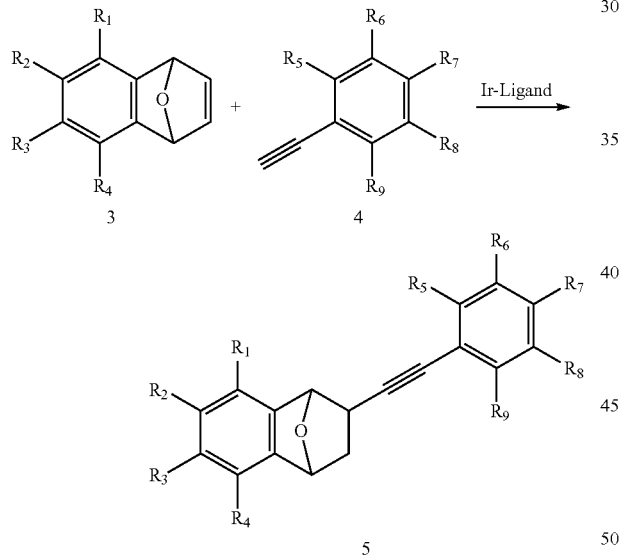

We are continuously interested in the asymmetric reactions of norbornadienes and alkynes in recent years. The Ir-catalyzed reaction between oxabenzonorbornadienes and alkynes are quite sensitive to the ligands selected. Previously in Fan, Bao-Min, Xiao-Jiao Li, Fang-Zhi Peng, Hong-Bin Zhang, Albert S. C. Chan, and Zhi-Hui Shao. "Ligand-Controlled Enantioselective [2+2] Cycloaddition of Oxabicyclic Alkenes with Terminal Alkynes Using Chiral Iridium Catalysts." *Organic Letters* 12.2 (2010): 304-06, the content of which is incorporated herein by reference in its entirety; it is reported that the complex of iridium and chiral Xylyl-phanephos can be served as catalyst for the [2+2] cycloaddition of oxabenzonorbornadienes with terminal alkynes, and the cyclobutene ring systems can be constructed in a single step in up to 99% ee. Herein in another embodiment of the present invention, we use other biaryl diphosphine ligands to finish the asymmetric additions of terminal alkynes to the C=C double bonds of oxabenzonorbornadienes without any [2+2] cycloaddition products obtained.

Many chiral diphosphine ligands (Scheme 3, 6-14) can generate the catalyst with $[Ir(COD)Cl]_2$ for the hydroalkynylation reactions of oxabenzonorbornadienes. The data in Table 1 showed the reaction of oxabenzonorbornadiene 3a and phenylacetylene 4a (2 equiv) in the presence of Ir complexes generated by $[Ir(COD)Cl]_2$ and diphosphine ligands.

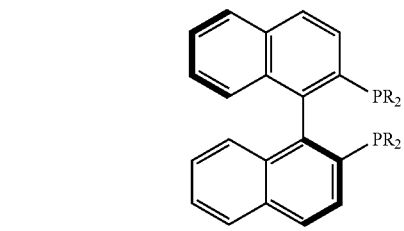

6 R = $C_6H_5^-$
7 R = 4-$CH_3$-$C_6H_4^-$
8 R = 3,5-$(CH_3)_2C_6H_3^-$

9

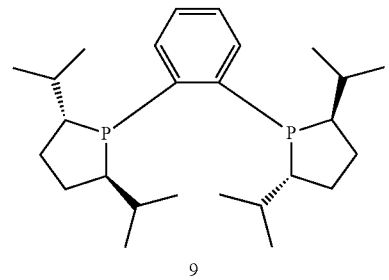

10 R = $C_6H_5^-$
11 R = 3,5-$(CH_3)_2$-$C_6H_3$-

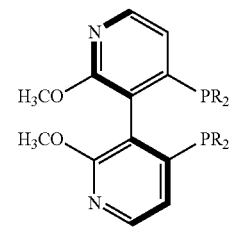

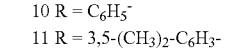

12

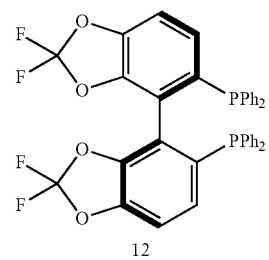

13

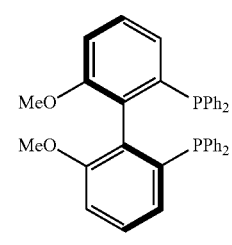

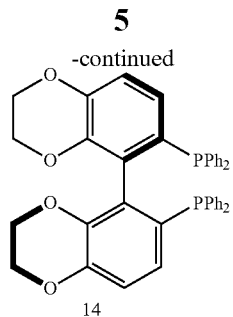

14

Scheme 3 ligands used in the addition of terminal alkynes to 7-oxabicyclic alkenes including (S)-BINAP 6, (S)-Tol-BINAP 7, (S)-Xyl-BINAP 8, (R, R)-i-Pr-DUPHOS 9, (S)-P-PHOS 10, (S)-Xyl-P-PHOS 11, (R)-DIFLUORPHOS 12, (S)-MeO-BIPHEP 13 and (R)-Synphos 14.

From Table 1, it can be seen that (S)-BINAP 6, (S)-Tol-BINAP 7 and (S)-Xyl-BINAP 8 all gave moderate to good yield (64-80%) but moderate enantioselectivity (38-48% ee) (entry 1-3). (R, R)-i-Pr-DUPHOS 9 was not as efficient as other biaryl diphosphine chiral ligands in this reaction (entry 4). When (S)-P-PHOS 10, (S)-Xyl-P-PHOS 11, (R)-DIFLUORPHOS 12, (S)-MeO-BIPHEP 13 and (R)-Synphos 14 were employed, the desired product 5aa was obtained in good yields and better enantioselectivities (entries 5-9). It could be seen that (R)-Synphos 14 resulted the best enantioselectivity (73% ee). Thus, [Ir(COD)Cl]$_2$ in combination with (R)-Synphos 14 was chosen to investigate temperature effect. The reaction at 70° C. afforded relatively higher enantioselectivity (77% ee) and 63% yield (entry 10). When the reaction was carried at 50° C., same enantioselectivity (76% ee) but lower yield (47%) was obtained (entry 11). Room temperature resulted in a sluggish reaction (entry 12).

The reaction was not sensitive to solvents. Many other solvents such as tetrahydrofuran (THF), dimethyl ether (DME), toluene, ethyl acetate (EtOAc), dioxane, acetonitrile (CH$_3$CN) and isopropanol (i-PrOH) were also effective in this reaction.

TABLE 1

Iridium-catalyzed asymmetric addition of phenylacetylene 4a to 7-oxabenzonorbornadiene 3a with different chiral ligands.[a] DCE stands for dichloroethene.

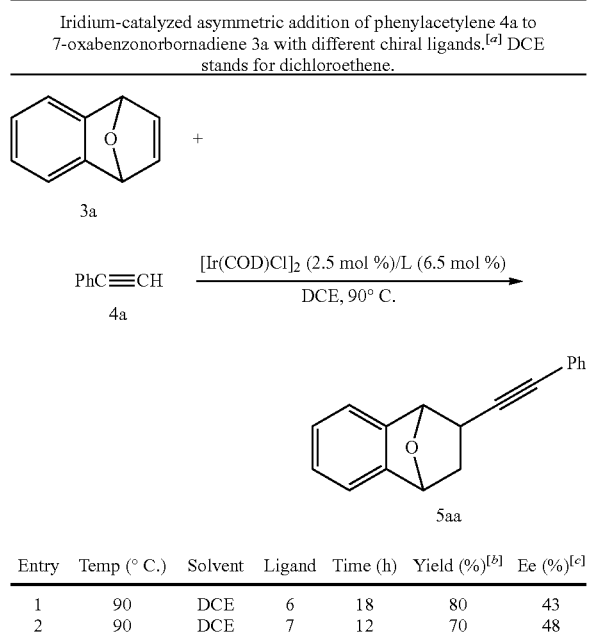

| Entry | Temp (° C.) | Solvent | Ligand | Time (h) | Yield (%)[b] | Ee (%)[c] |
|---|---|---|---|---|---|---|
| 1 | 90 | DCE | 6 | 18 | 80 | 43 |
| 2 | 90 | DCE | 7 | 12 | 70 | 48 |
| 3 | 90 | DCE | 8 | 12 | 64 | 38 |
| 4 | 90 | DCE | 9 | 18 | 22 | <10 |
| 5 | 90 | DCE | 10 | 18 | 51 | 67 |
| 6 | 90 | DCE | 11 | 18 | 69 | 66 |
| 7 | 90 | DCE | 12 | 18 | 48 | 61 |
| 8 | 90 | DCE | 13 | 12 | 68 | 70 |
| 9 | 90 | DCE | 14 | 6 | 67 | 73 |
| 10 | 70 | DCE | 14 | 24 | 63 | 77 |
| 11 | 50 | DCE | 14 | 60 | 47 | 76 |
| 12 | rt | DCE | 14 | 60 | <10 | / |

[a]Reaction conditions: 3a (0.3 mmol), 3a:4a:[Ir(COD)Cl]$_2$:Ligand (1:2:0.025:0.065), in solvent (2 mL) at 70° C. under Ar$_2$ for indicated period of time.
[b]Isolated yield by column chromatography.
[c]Determined by chiral high performance liquid chromatography (HPLC) using a Chiralcel OD-H column.

Other iridium pre-catalysts in combination with ligand 14 were also investigated in the invention. Ir(I)(COD)(acac) gave relatively lower enantiomeric excess (72%) but higher yield (79% yield) under the same conditions. Ir(III)(C$_7$H$_8$)$_3$ (acac) showed lower catalytic activity.

The results of the addition of a variety of terminal alkynes 4a-k to oxabenzonorbornadiene 3a in the presence of [Ir(COD)Cl]$_2$ (2.5% mol) and (R)-Synphos 14 (6.5% mol) in dichloroethene (DCE) at 70° C. are summarized in Table 2. Generally, all terminal aromatic alkynes reacted with 3a smoothly to provide the corresponding adducts in good yields and high enantioselectivities (entries 1-10). The electronic properties of the substituents for aromatic rings of terminal alkynes 4b-j are well tolerated by this addition reaction. In particular, the terminal alkyne with —CH$_2$OH on aromatic ring afforded good enantioselectivity (75% ee) and moderate yield (54%) (entry 7). In addition, the aliphatic terminal alkyne 4k also gave 61% yield and 68% ee value (entry 11).

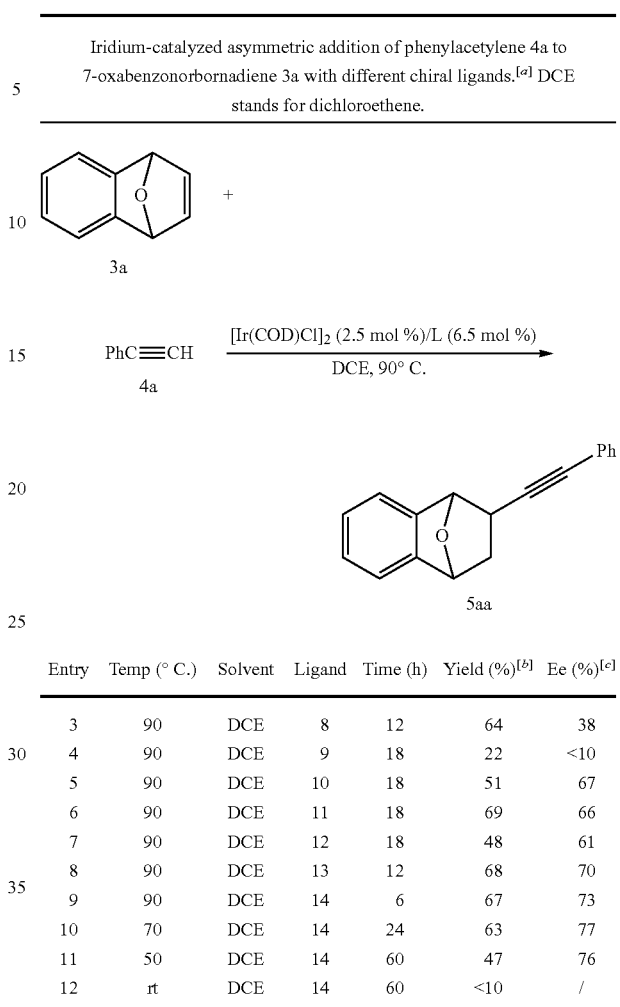

TABLE 2

Iridium-catalyzed asymmetric addition of various alkynes 4a-k to 7-oxabenzonorbornadiene 3a.[a]

3a + RC≡CH (4a-k) → [Ir(COD)Cl]₂ (2.5 mol %)/14 (6.5 mol %), DCE, 70° C. → 5aa-5ak

| Entry | Alkyne | | Time (h) | Yield (%)[b] | Ee (%)[c] |
|---|---|---|---|---|---|
| 1 | C₆H₅ | a | 24 | 63 | 77 |
| 2 | 4-OMe-C₆H₄ | b | 24 | 87 | 78 |
| 3 | 4-NMe₂-C₆H₄ | c | 10 | 90 | 74 |
| 4 | 4-Me-C₆H₄ | d | 30 | 90 | 69 |
| 5 | 4-Br-C₆H₄ | e | 60 | 82 | 62 |
| 6 | 4-F-C₆H₄ | f | 60 | 89 | 75 |
| 7 | 4-CH₂OH-C₆H₄ | g | 15 | 54 | 73 |
| 8 | 4-CF₃-C₆H₄ | h | 60 | 51 | 73 |
| 9 | 3-OMe-C₆H₄ | i | 48 | 76 | 74 |
| 10 | 2-OMe-C₆H₄ | j | 36 | 93 | 75 |
| 11 | PhCH₂CH₂C≡CH | k | 48 | 61 | 67 |

[a]Reaction conditions: 3a (0.3 mmol), 3a:4a-k:[Ir(COD)Cl]₂:(R)-Synphos (1:1.5:0.025:0.065), in DCE (2 mL) at 70° C. under Ar₂ for indicated period of time.
[b]Isolated yield by column chromatography.
[c]Determined by chiral HPLC using a Chiralcel OD-H or AD-H column.

To extend the scope of substrates, substituted oxabenzonorbornadiene derivatives 3b-g were examined. As shown in Table 3, the addition of oxabenzonorbornadienes 3b-g with 4-methoxy-phenylacetylene 4b proceeded smoothly to afford the corresponding adducts in good yields and enantioselectivities (entries 1-6, Table 3).

TABLE 3

Iridium-catalyzed asymmetric addition of 4-methoxy-phenylacetylene 4b to substituted oxabenzonorbornadiene derivatives 3b-g.[a]

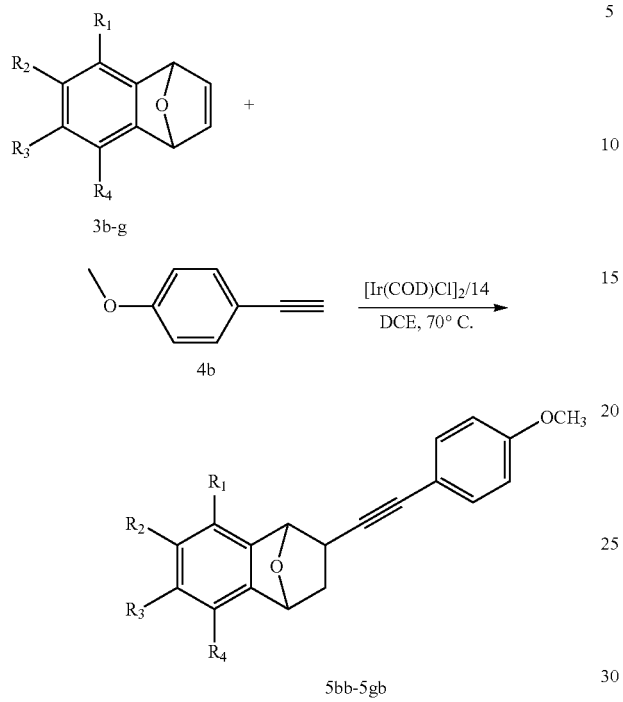
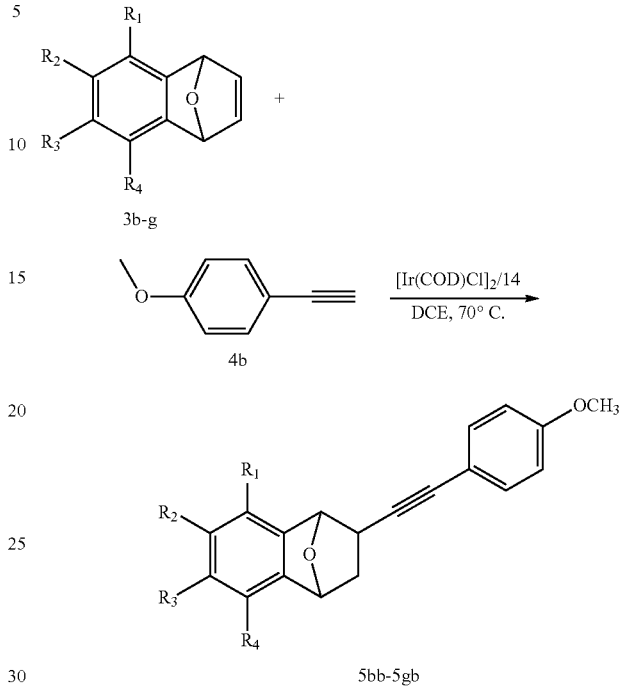

| Entry | Substituted oxobenzonorbornadiene | | Time (h) | Yield (%)[b] | Ee (%)[c] |
|---|---|---|---|---|---|
| 1 | OMe / OMe | b | 19 | 92 | 67 |
| 2 | (dimethyl) | c | 19 | 81 | 75 |
| 3 | Br / Br | d | 19 | 84 | 85 |
| 4 | MeO / MeO | e | 60 | 66 | 76 |
| 5 | (dioxine-fused) | f | 65 | 75 | 73 |
| 6 | (methylenedioxy-fused) | g | 46 | 70 | 72 |

[a]Reaction conditions: 3a (0.3 mmol), 3a:4a:[Ir(COD)Cl]$_2$: (R)-Synphos (1:1.5:0.025:0.065), in DCE (2 mL) at 70° C. under Ar$_2$ for indicated period of time.
[b]Isolated yield by column chromatography.
[c]Determined by chiral HPLC using a Chiralcel OD-H, OJ-H or AD-H column.

The iridium-catalyzed asymmetric hydroalkynylation reactions of oxabenzonorbornadienes were developed with good yields and moderate enantioselectivities. Further biological activities screening was based on the racemic products catalyzed by racemic BINAP.

To determine the cytotoxicity of the compounds, the IC50 on HTC-116, HT-29, MCF-7, and MDA-MB-231 cell lines was determined. As the results shown in Table 4, 5bb had strong cell growth-inhibiting effects against MCF-7 and MDA-MB-231 cells for which IC50 values are below or near 10 μM. 5bb also can inhibit cell growth of HTC-116 cells with IC50 value of 16.57 μM.

TABLE 4

Cytotoxicity of compounds against Cancer Cell Lines

| Compound | HTC-116 | HT-29 | MCF-7 | MDA-MB-231 |
|---|---|---|---|---|
| 5bb | 16.57 | 29.01 | 9.83 | 10.77 |
| 5eb | — | — | 25.25 | 41.44 |

Results are expressed as IC$_{50}$ values in μM.

Results are expressed as IC$_{50}$ values in μM.

Experimental Section

Procedure of Synthesis

Under the protection of $Ar_2$, $[Ir(COD)Cl]_2$ (5.1 mg, 0.0075 mmol), (R)-BisbenzodioxanPhos 14 (12.5 mg, 0.0195 mmol) and 1.0 mL 1,2-dichloroethane were added to a Schlenk tube. The solution obtained was stirred at room temperature. 30 minutes later, 7-Oxa-benzanorbornadiene 3a (43.2 mg, 0.3 mmol) and another 1.0 mL 1,2-dichloroethane were added, and the stirring was continued for additional 20 minutes. After the addition of phenylacetylene 4a (61.2 mg, 0.6 mmol), the Schlenk tube was sealed with a rubber septum and moved to an oil bath. The mixture was stirred at 70° C. (bath temperature) until the reaction was completed. After vacuum evaporation of the reaction solvent, the residue was purified by column chromatography on silica gel eluting with Hexane/Ethyl Acetate (15:1), and a white solid was obtained as product 5aa (46.5 mg, 63% yield). The enantioselective excess of the product was determined to be 77% by chiral HPLC.

Cytotoxicity Assay

All compounds were dissolved in dimethyl sulfoxide (DMSO) to make stock solutions and further diluted in culture medium for the experiments. Human cancer cell lines, including two human colorectal carcinoma cell lines (HTC-116 and HT-29) and two human breast adenocarcinoma cell lines (MCF-7 and MDA-MB-231), were cultured in RPMI 1640 medium, containing 10% fetal bovine serum and 1% antibiotics (Penicillin and strep). The cell lines were cultured at 37° C. in a humidified environment containing 5% CO2. To determine the effects of the compounds on cell viability, a standard colorimetric 3-(4,5-dimethylthiazol-2-yl)-2,5-diphenyltetrazolium bromide (MTT) assay was used to test the cell number. Cells were plated in a 96-well plate (4×103 cells/well) and allowed to attach overnight. After the recovery, cells were treated with 1.56, 3.125, 6.25, 12.5, 25, 50, 100 μM of compounds in culture medium for 48 hrs. Then, 20 μL of MTT (5 mg/mL stock in PBS) per well was added into the medium (200 μL) and incubated for 4 hrs at 37° C. Finally, the culture media was removed and 200 μL of DMSO were added to dissolve the purple formazan crystals. Absorbance of the solution was measured using microplate reader spectrophotometer (Bio-Rad Laboratories, Inc., Hercules, Calif.), at a wavelength of 570 nm.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extend. All publications recited herein are hereby incorporated by reference in their entirety.

What we claim:

1. A method of synthesizing norcantharidin analogues comprising the structure of compound 5:

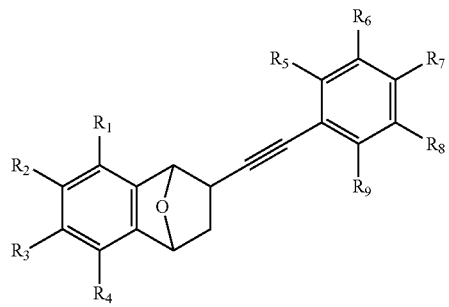

wherein $R_1$, $R_2$, $R_3$, $R_4$ are selected from the group consisting of hydrogen, halogen, alkyl, alkenyl, alkynyl, hydroxyl, alkoxyl, amine, nitro, alkylthio and heteroalkyl, and wherein $R_5$, $R_6$, $R_7$, $R_8$, $R_9$ are selected from the group consisting of hydrogen, halogen, alkyl, alkenyl, alkynyl, hydroxyl, alkoxyl, amine, nitro, nitrile, alkylthio, trifluoromethyl, alkyl sulfonyl and aryl sulfonyl, the method comprising the step of alkynylation of oxabenzonorbornadienes in the presence of a catalyst including a transition metal compound and a biaryl diphosphine ligand selected from the group consisting of:

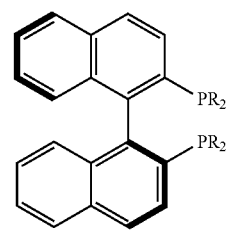

6 R = $C_6H_5^-$
7 R = 4-$CH_3$-$C_6H_4^-$
8 R = 3,5-$(CH_3)_2C_6H_3^-$

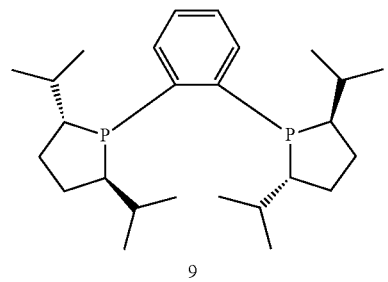

9

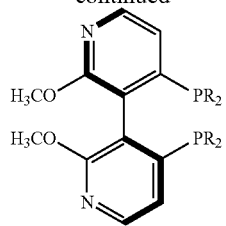

10 R = C₆H₅⁻
11 R = 3,5-(CH₃)₂-C₆H₃-

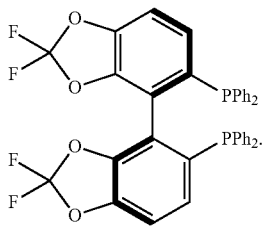

12

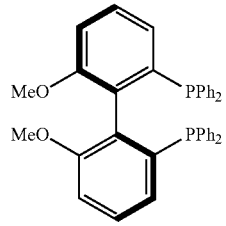

13

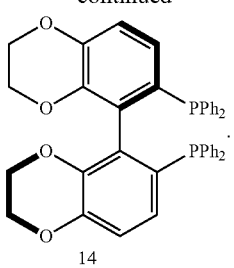

14

2. A method according to claim 1, wherein the transition metal compound is an Iridium compound.

3. A method according to claim 2, wherein the Iridium compound is selected from the group consisting of Ir(I)(COD)Cl, Ir(I)(COD)(acac) and Ir(III)(C7H8)3(acac).

4. A method according to claim 1, wherein the step of alkynylation is carried out in the presence of a solvent, the solvent is selected from the group consisting of dichloroethene, tetrahydrofuran, dimethyl ether, toluene, ethyl acetate, isopropanol and a mixture thereof.

5. A method for the treatment of cancer tumors comprising treating cancer cells with compound 5 according to any one of the above claims. for the treatment of cancer tumor.

6. The method according to claim 5 wherein said cancer tumors comprise colorectal carcinoma and breast adenocarcinoma.

* * * * *